United States Patent
Monaghan et al.

(10) Patent No.: US 12,237,084 B2
(45) Date of Patent: Feb. 25, 2025

(54) SYSTEM FOR ASSESSING AND MITIGATING POTENTIAL SPREAD OF INFECTIOUS DISEASE AMONG DIALYSIS PATIENTS

(71) Applicant: Fresenius Medical Care Holdings, Inc., Waltham, MA (US)

(72) Inventors: Caitlin Kelly Monaghan, Arlington, MA (US); Peter Kotanko, New York, NY (US); John Larkin, Hudson, MA (US); Jeffrey Hymes, Nashville, TN (US); Kathleen Belmonte, Concord, MA (US); Len Usvyat, Boston, MA (US); Ines A. Dahne-Steuber, Marietta, GA (US); Franklin W. Maddux, Lincoln, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 529 days.

(21) Appl. No.: 17/226,021

(22) Filed: Apr. 8, 2021

(65) Prior Publication Data
US 2021/0319905 A1 Oct. 14, 2021

Related U.S. Application Data

(60) Provisional application No. 63/008,626, filed on Apr. 10, 2020.

(51) Int. Cl.
*G16H 50/30* (2018.01)
*G16H 20/00* (2018.01)
(Continued)

(52) U.S. Cl.
CPC ............. *G16H 50/30* (2018.01); *G16H 20/00* (2018.01); *G16H 20/40* (2018.01); *G16H 50/20* (2018.01); *G16H 50/70* (2018.01); *G16H 50/80* (2018.01)

(58) Field of Classification Search
CPC ...................................................... A61B 5/00
See application file for complete search history.

(56) References Cited

U.S. PATENT DOCUMENTS

| 9,801,993 B2 | 10/2017 | Barrett et al. |
| 2009/0112102 A1* | 4/2009 | Roeher ............ A61M 1/36 |
| | | 600/485 |

(Continued)

FOREIGN PATENT DOCUMENTS

| CN | 109656918 A * | 4/2019 | ............. G06N 3/084 |
| JP | 6418624 B2 * | 11/2018 | |
| WO | WO-2006113987 A1 * | 11/2006 | ......... G06F 19/3431 |

OTHER PUBLICATIONS

L. Torlay et al., Machine learning-XGBoost analysis of language networks to classify patients with epilepsy, Apr. 22, 2017, Brain Informatics vol. 4, pp. 159-169 (Year: 2017).*

(Continued)

*Primary Examiner* — Evangeline Barr
*Assistant Examiner* — Austin Rivoire Amacher
(74) *Attorney, Agent, or Firm* — Leydig, Voit & Mayer, Ltd.

(57) ABSTRACT

A method for mitigating the spread of infectious diseases among dialysis patients is provided. The method comprises: receiving, by a prediction system and from a medical facility, individual treatment data indicating dialysis treatment information associated with a patient undergoing dialysis treatment; receiving, by the prediction system and from a blood testing laboratory, individual lab data indicating blood analysis information associated with the patient;

(Continued)

determining, by the prediction system, disease analysis results for the patient based on inputting the individual treatment data and the individual lab data into a disease prediction machine learning (ML) model, wherein the disease analysis results indicate a likelihood of the patient being infected with a contagious disease; and providing, by the prediction system and to the medical facility, instructions indicating one or more responsive actions based on the disease analysis results.

18 Claims, 6 Drawing Sheets

(51) Int. Cl.
*G16H 20/40* (2018.01)
*G16H 50/20* (2018.01)
*G16H 50/70* (2018.01)
*G16H 50/80* (2018.01)

(56) References Cited

U.S. PATENT DOCUMENTS

| | | | |
|---|---|---|---|
| 2013/0191158 A1* | 7/2013 | Fillmore | G16H 50/30 705/3 |
| 2014/0167917 A2* | 6/2014 | Wallace | G16H 40/67 340/10.1 |
| 2015/0149096 A1* | 5/2015 | Soykan | A61B 5/021 702/19 |
| 2015/0213224 A1* | 7/2015 | Amarasingham | G16H 50/30 705/2 |
| 2019/0057774 A1* | 2/2019 | Velez | G16H 50/20 |
| 2020/0005947 A1 | 1/2020 | Blanchard et al. | |
| 2020/0065679 A1* | 2/2020 | Javeri | G01C 21/3617 |
| 2020/0113505 A1* | 4/2020 | Clingman | A61B 5/4312 |
| 2020/0176112 A1* | 6/2020 | Sati | G06F 40/30 |

OTHER PUBLICATIONS

Ping-Nam Wong, Siu-Ka Mak, Kin-Yee Lo, Gensy M.W Tong, Yuk Wong, Chi-Leung Watt, Andrew K.M Wong, Clinical presentation and outcome of severe acute respiratory syndrome in dialysis patients, American Journal of Kidney Diseases 42(5):p. 1075-1081, Nov. 2003 (Year: 2003).*
R. Saran et al. Longer treatment time and slower ultrafiltration in hemodialysis: Associations with reduced mortality in the DOPPS, Kidney International, vol. 69, Issue 7, 2006 (Year: 2006).*
Saran et al., Longer treatment time and slower ultrafiltration in hemodialysis: Associations with reduced mortality in the DOPPS, Kidney International, vol. 69, Issue 7, 2006, pp. 1222-1228 (Year: 2006).*
International Patent Application No. PCT/US2021/026455, International Search Report (Jul. 26, 2021).
Adams et al. "Population-Based Estimates of Chronic Conditions Affecting Risk for Complications from Coronavirus Disease, United States" *Emerg. Infect. Dis.*, vol. 26(8), 1831-1833 (Aug. 2020).
Ahamad et al., "A Machine Learning Model to Identify Early Stage Symptoms of SARS-Cov-2 Infected Patients," *Expert Syst. Appl.* vol. 160, 113661 (2020).
Alimadadi et al., "Artificial Intelligence and Machine Learning to Fight COVID-19," *Physiol. Genomics*, vol. 52, 200-202 (2020).
Anand et al., "Prevalence of SARS-CoV-2 Antibodies in a large nationwide sample of patients on dialysis in the USA: a cross-sectional study," *Lancet*, vol. 396, 1335-1344 (2020).
Banerjee et al., "Use of Machine Learning and Artificial Intelligence to predict SARS-CoV-2 infection from Full Blood Counts in a population," *Int. Immunopharmacol.* vol. 86, 106705 (2020).
Basile et al., "Recommendations for the Prevention, Mitigation and Containment of the Emerging SARS-CoV-2 (COVID-19) Pandemic in Haemodialysis Centres," *Nephrol. Dial. Transplant* (2020).
Bogoch et al., "Pneumonia of Unknown Aetiology in Wuhan, China: Potential for International Spread via Commercial Air Travel," *J. Travel Med.* (2020).
CDC COVID-19 Response Team, "Geographic Differences in COVID-19 Cases, Deaths, and Incidence—United States," MMWR Morb. Mortal Wkly. Rep., vol. 69(15), 465-471 (Apr. 17, 2020).
Chen et al., "XGBoost: A Scalable Tree Boosting System," *Proceedings of the 22nd ACM SIGKDD International Conference on Knowledge Discovery and Data Mining*. San Francisco, California, 785-794 (2016).
Cheng et al., "Kidney Disease is Associated with In-Hospital Death of Patients With COVID-19," *Kidney Int.*, vol. 97, 829-838 (2020).
COVID-19 Resource and Education Center, Fresenius Medical Care North America, https://lmcna.com/covid-19-resource-center/ (Apr. 15, 2021).
Du et al., "Predictors of Mortality for Patients with COVID-19 Pneumonia Caused by SARS-CoV-2: A Prospective Cohort Study," *Eur. Respir. J.* (2020).
ERACODA—"The Era-Edta COVID-19 Database for Patients on Kidney Replacement Therapy," ERAEDTA, https://www.era-edta.org/en/wpcontent/uploads/2020/04/ERACODA-Study-Report-2020-04-29.pdf (Apr. 29, 2020).
Feng et al., "A Novel Artificial Intelligence-Assisted Triage Tool to Aid in the Diagnosis of Suspected COVID-19 Pneumonia Cases in Fever Clinics," *Ann. Transl. Med.* (2021).
Fontana et al., "SARS-CoV-2 Infection in Dialysis Patients in Northern Italy: A Single-Centre Experience," *Clin. Kidney J.*, vol. 13, 334-339 (2020).
Gagliardi et al., "COVID-19 and the Kidney: From Epidemiology to Clinical Practice," *J. Clin. Med*, vol. 9 (2020).
Gallieni et al., "Delivering safe and effective hemodialysis in patients with suspected or confirmed COVID-19 infection: a single-center perspective from Italy," *Kidney360*: 10.34067/KID.0001782020 (2020).
Gedney, N., "Long-Term Hemodialysis During the COVID-19 Pandemic," *Clin. J. Am. Soc. Nephrol.*, vol. 15, 1073-1074 (Aug. 2020).
Guo et al., "Cardiovascular Implications of Fatal Outcomes of Patients With Coronavirus Disease" *JAMA Cardiol.*, vol. 5 (Jul. 2020).
Ikizler T.A., "COVID-19 and Dialysis Units: What Do We Know Now and What Should We Do?" *Am. J Kidney Dis.*, vol. 76 (Jul. 2020).
Jager et al., "Results from the ERAEDTA Registry Indicate a High Mortality Due to COVID-19 in Dialysis Patients and Kidney Transplant Recipients Across Europe," *Kidney Int.*, 1540-1548 (2020).
Kikuchi et al., "COVID-19 of Dialysis Patients in Japan: Current Status and Guidance on Preventive Measures," Ther. Apher. Dial., 24, 361-365 (2020).
Kliger et al., "Mitigating Risk of COVID-19 in Dialysis Facilities" *Clin. J. Am. Soc. Nephrol.*, vol. 15, 707-709 (2020).
Leung et al., "First-wave COVID-19 Transmissibility and Severity in China Outside Hubei After Control Measures, and Second-Wave Scenario Planning: A Modelling Impact Assessment," *Lancet*, vol. 395, 1382-1393 (2020).
Li et al., "Risk Factors for Severity and Mortality in Adult COVID-19 Inpatients in Wuhan," *J. Allergy Clin. Immunol.* vol. 146, 110-118 (2020).
Lundberg et al., "A Unified Approach to Interpreting Model Predictions," 31st Conference on Neural Information Processing Systems, Long Beach, CA, USA (2017).
Lundberg et al., "From Local Explanations to Global Understanding With Explainable AI for Trees," *Nature Machine Intelligence*, vol. 2, 56-67 (Jan. 2020).
Ma et al., "COVID-19 in Hemodialysis (HD) Patients: Report From One HD Center in Wuhan China ," medRxiv: 2020.2002.2024. 20027201 (2020).
McCall, B., "COVID-19 and artificial intelligence: protecting healthcare workers and curbing the Spread," *Lancet Digit. Health*, vol. 2, e166-e167 (Apr. 2020).

(56) References Cited

OTHER PUBLICATIONS

Meng et al., "Development and utilization of an intelligent application for aiding COVID-19 diagnosis," medRxiv: 2020.2003.2018.20035816 (2020).

Mokrzycki et al., "Management of hemodialysis patients with suspected or confirmed COVID-19 infection: perspective of two nephrologists in the United States," *Kidney360*: 10.34067/KID.0001452020 (2020).

Monaghan et al., "Machine Learning for Prediction of Patients on Hemodialysis with an Undetected SARS-CoV-2 Infection," *Kidney360*. vol. 2, 456-468 (2021).

Neumann, M.E., "Latest data show 305 dialysis patient deaths due to COVID-19 in the US," https://www.healio.com/nephrology/infectioncontrol/news/online/%7B3a263aa9-ad59-4c3f-aab7-07b8395508e5%7D/latest-data-show-305-dialysis-patient-deaths-due-to-covid-19-in-the-us (Apr. 14, 2020).

Niiler, E., "An AI Epidemiologist Sent the First Warnings of the Wuhan Virus," Wired, https://www.wired.com/story/ai-epidemiologist-wuhan-public-health-warnings/ (Jan. 25, 2020).

Roncon et al., "Diabetic patients with COVID-19 infection are at higher risk of ICU admission and poor short-term outcome," *J. Clin. Virol.*, 127 (2020).

Saito et al., "The precision-recall plot is more informative than the ROC plot when evaluating binary classifiers on imbalanced datasets," PLoS One, 10: e0118432 (Mar. 4, 2015).

Shaikh et al., "Prolonged SARS-CoV-2 Viral RNA Shedding and IgG Antibody Response to SARS-CoV-2 in Patients on Hemodialysis," *Clinical Journal of the American Society of Nephrology*, vol. 16, 290-292 (2021).

Shapley L.S., "A Value for n-Person Games," In: H. W. Kuhn and A. W. Tucker, Eds., *Contributions to the Theory of Games II. Annals of Mathematics Studies*, Princeton University Press, Princeton, N.J., 28: 307-317 (1953).

Siordia J.A., Jr., "Epidemiology and clinical features of COVID-19: A review of current literature," *J. Clin. Virol.*, vol. 127 (2020).

Song et al., "COVID-19 early warning score: a multi-parameter screening tool to identify highly suspected patients," medRxiv: 2020.2003.2005.20031906 (2020).

Štrumbelj et al., "Explaining prediction models and individual predictions with feature Contributions," *Knowl. Inf. Syst.*, 41, 647-665 (2014).

United States Renal Data System, "Epidemiology of kidney disease in the United States," *National Institutes of Health, National Institute of Diabetes and Digestive and Kidney Diseases*, Bethesda, MD (2019).

Usvyat et al., "Circadian variations in body temperature during dialysis," *Nephrol. Dial Transplant*, 27, 1139-1144 (2012).

Vaishya et al., "Artificial Intelligence (AI) applications for COVID-19 Pandemic," *Diabetes Metab. Syndr.* vol. 14, 337-339 (2020).

Wang, H., "Maintenance Hemodialysis and Coronavirus Disease 2019 (COVID-19): Saving Lives With Caution, Care, and Courage," *Kidney Med.* vol. 2 (May/Jun. 2020).

Wynants et al., "Prediction models for diagnosis and prognosis of covid-19: systematic review and critical appraisal," *BMJ*, 369, m1328 (2020).

Xiong et al., "Clinical Characteristics of and Medical Interventions for COVID-19 in Hemodialysis Patients in Wuhan, China," *J. Am. Soc. Nephrol.*, vol. 31, 1387-1397 (2020).

Xu et al., "Beware of the second wave of COVID-19," *Lancet*, vol. 395 (2020).

Zhou et al., "Clinical course and risk factors for mortality of adult inpatients with COVID-19 in Wuhan, China: a retrospective cohort study," *Lancet*, vol. 395, 1054-1062 (2020).

\* cited by examiner

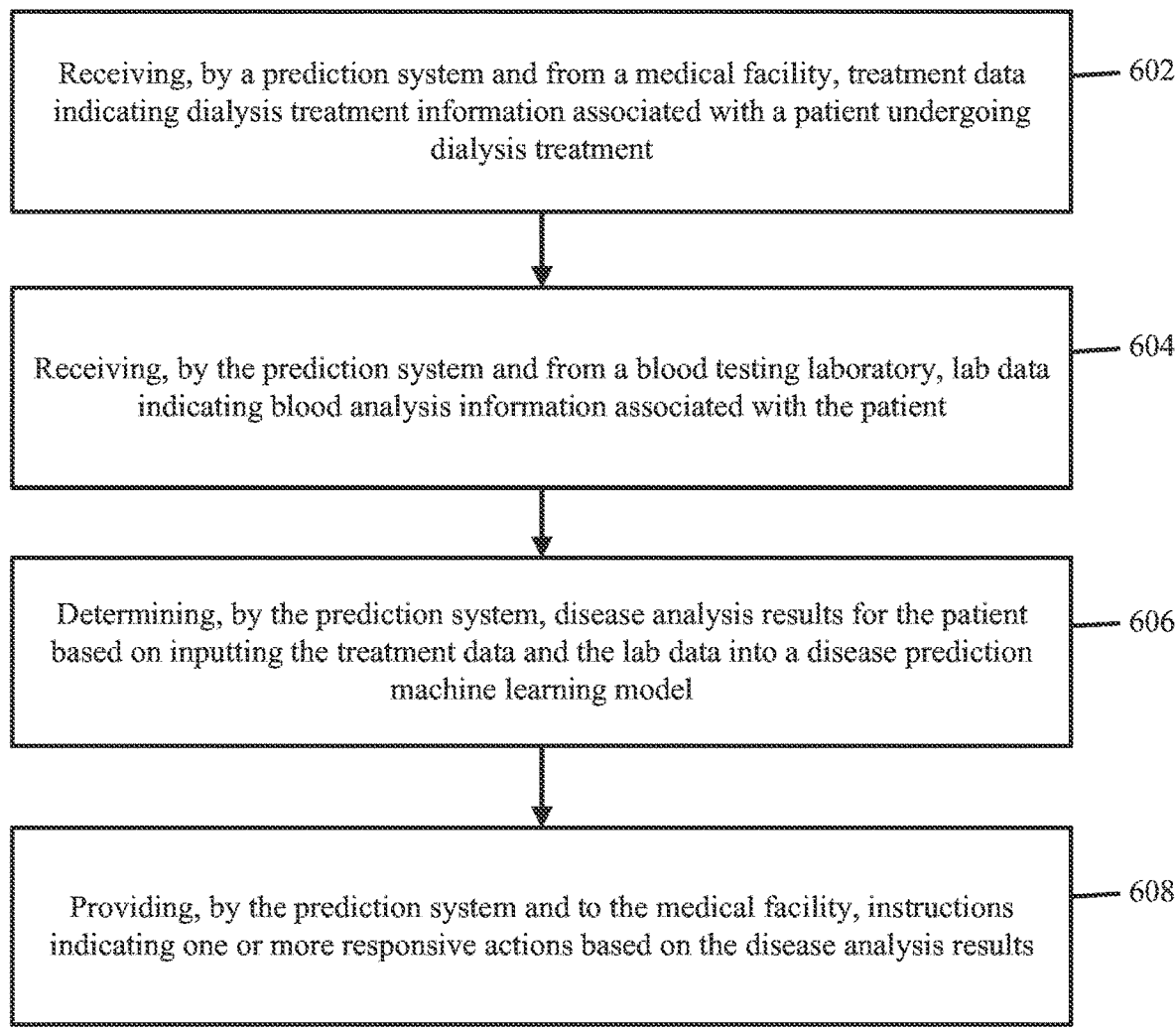

SYSTEM FOR ASSESSING AND MITIGATING POTENTIAL SPREAD OF INFECTIOUS DISEASE AMONG DIALYSIS PATIENTS

CROSS-REFERENCE TO RELATED APPLICATIONS

This application claims priority to U.S. Provisional Patent Application Ser. No. 63/008,626, filed Apr. 10, 2020, entitled "SYSTEM FOR ASSESSING AND MITIGATING POTENTIAL SPREAD OF INFECTIOUS DISEASE AMONG DIALYSIS PATIENTS," the contents of which application is expressly incorporated by reference herein.

FIELD

The disclosure generally relates to healthcare-related systems, devices, and methods.

BACKGROUND

Patients with kidney failure or partial kidney failure typically undergo dialysis treatment in order to remove toxins and excess fluids from their blood. The 2019 coronavirus disease (COVID-19) pandemic has made the hardships of patients undergoing dialysis treatment even more drastic. For instance, the COVID-19 pandemic is and has been challenging the world's healthcare systems including bringing complexities for patients undergoing these dialysis treatments and this is especially true for patients with end stage kidney disease (ESKD). In the United States, dialysis patients visit dialysis clinics as often as three times per week and most ESKD patients are treated by outpatient hemodialysis (HD) where social distancing may be difficult and heightened infection control measures are required (e.g. temperature screenings, universal masking, and isolation treatments/shifts/clinics).

ESKD patients are typically older and have multiple comorbidities, placing the population at higher risk for requiring intensive care and dying if affected by COVID-19. Early reports from the United States show an 11% COVID-19 mortality in ESKD, which is higher than the 3% COVID-19 mortality shown in the national population. This is not unexpected with reports from Asia and Europe suggesting a 16% to 23% COVID-19 mortality in ESKD. Albeit the high mortality rate, an impaired immune response may render dialysis patients more frequently asymptomatic when infected by COVID-19. In both the general and ESKD populations, the most prevalent symptoms of COVID-19 are fever (11%-66% in dialysis; 82% in general population) and cough (37%-57% in dialysis; 62% in general population). The less frequent occurrence of signs and symptoms indicative of COVID-19 in dialysis patients may make the COVID-19 outbreak even more challenging to manage especially for dialysis providers in attempting to prevent the spread of the disease to other patients undergoing dialysis.

Dialysis providers routinely capture patient/clinical data (e.g., treatment data) for each patient during their dialysis treatment. Further, dialysis patients typically undergo periodic blood draws (e.g., once a month) from which lab data is obtained for each patient to monitor the patient's health and evaluate whether their treatment plan is working or whether it needs to be adjusted.

Accordingly, the robust data collected during dialysis treatments (generally thrice weekly) and/or periodic blood draws may provide opportunities to detect whether a patient has COVID-19 and/or other diseases. It is with respect to these and other considerations that the present improvements may be useful.

SUMMARY

This summary is provided to introduce a selection of concepts in a simplified form that are further described below. This summary is not intended to necessarily identify key features or essential features of the present disclosure. The present disclosure may include the following various aspects and embodiments.

In an exemplary embodiment, the present application provides a method for mitigating the spread of infectious diseases among dialysis patients. The method comprises: receiving, by a prediction system and from a medical facility, individual treatment data indicating dialysis treatment information associated with a patient undergoing dialysis treatment; receiving, by the prediction system and from a blood testing laboratory, individual lab data indicating blood analysis information associated with the patient; determining, by the prediction system, disease analysis results for the patient based on inputting the individual treatment data and the individual lab data into a disease prediction machine learning (ML) model, wherein the disease analysis results indicate a likelihood of the patient being infected with a contagious disease; and providing, by the prediction system and to the medical facility, instructions indicating one or more responsive actions based on the disease analysis results.

In some instances, the method further comprises: receiving, by the prediction system, group treatment data indicating dialysis treatment information associated with a plurality of patients undergoing the dialysis treatment; receiving, by the prediction system, group lab data indicating blood analysis information associated with the plurality of patients undergoing the dialysis treatment; and training, by the prediction system, the disease prediction ML model based on the group treatment data and the group lab data.

In some examples, the method further comprises: receiving, by the prediction system, group physician data indicating clinical or treatment notes associated with the plurality of patients undergoing the dialysis treatment, wherein training the disease prediction ML model is further based on the group physician data.

In some variations, the method further comprises: receiving, by the prediction system and from the medical facility, individual physician data indicating clinical or treatment notes associated with the patient undergoing the dialysis treatment, and wherein determining the disease analysis results is further based on inputting the individual physician data into the disease prediction ML model.

In some instances, the method further comprises: obtaining, by the prediction system, group patient data indicating patient demographics and history associated with the plurality of patients undergoing the dialysis treatment, wherein training the disease prediction ML model is further based on the group patient data.

In some examples, the method further comprises: receiving, by the prediction system, individual patient data indicating clinical or treatment notes associated with the patient undergoing the dialysis treatment, and wherein determining the disease analysis results is further based on inputting the individual patient data into the disease prediction ML model.

In some variations, the method further comprises: obtaining, by the prediction system, geographical disease data indicating new reported cases of the contagious disease within a geographical area associated with the patient, wherein training the disease prediction ML model is further based on the geographical disease data.

In some instances, the geographical disease data indicates the new reported cases of the medical facility.

In some examples, the group treatment data is associated with the medical facility. The method further comprises: training, by the prediction system, a second disease prediction ML model for a second medical facility that is different from the medical facility; and selecting to use the disease prediction ML model for the patient based on receiving the individual treatment data from the medical facility.

In some variations, the method further comprises: receiving, from the medical facility, feedback indicating one or more inaccuracies with the disease prediction ML model; and re-training the disease prediction ML model based on the feedback, wherein determining the disease analysis results for the patient is based on inputting the individual treatment data and the individual lab data into the re-trained disease prediction machine learning (ML) model.

In some instances, the disease prediction ML model is an extreme Gradient Boosting (XGBoost) model or a deep learning model.

In some examples, the one or more responsive actions comprise adjusting patient scheduling to re-assign the patient to an isolation shift for a future dialysis treatment, initiating a treatment regimen for the patient, allocating personal protective equipment (PPE) for the medical facility, or adjusting dialysis treatment parameters for the patient.

In another exemplary embodiment, a prediction system is provided. The prediction system comprises one or more processors; and a non-transitory computer-readable medium having processor-executable instructions stored thereon. The processor-executable instructions, when executed by the one or more processors, facilitate: receiving, from a medical facility, individual treatment data indicating dialysis treatment information associated with a patient undergoing dialysis treatment; receiving, from a blood testing laboratory, individual lab data indicating blood analysis information associated with the patient; determining disease analysis results for the patient based on inputting the individual treatment data and the individual lab data into a disease prediction machine learning (ML) model, wherein the disease analysis results indicate a likelihood of the patient being infected with a contagious disease; and providing, to the medical facility, instructions indicating one or more responsive actions based on the disease analysis results.

In some instances, the processor-executable instructions, when executed by the one or more processors, further facilitate: receiving group treatment data indicating dialysis treatment information associated with a plurality of patients undergoing the dialysis treatment; receiving group lab data indicating blood analysis information associated with the plurality of patients undergoing the dialysis treatment; and training the disease prediction ML model based on the group treatment data and the group lab data.

In some examples, the processor-executable instructions, when executed by the one or more processors, further facilitate: receiving group physician data indicating clinical or treatment notes associated with the plurality of patients undergoing the dialysis treatment, wherein training the disease prediction ML model is further based on the group physician data.

In some variations, the processor-executable instructions, when executed by the one or more processors, further facilitate: receiving, from the medical facility, individual physician data indicating clinical or treatment notes associated with the patient undergoing the dialysis treatment, and wherein determining the disease analysis results is further based on inputting the individual physician data into the disease prediction ML model.

In some instances, the processor-executable instructions, when executed by the one or more processors, further facilitate: obtaining group patient data indicating patient demographics and history associated with the plurality of patients undergoing the dialysis treatment, wherein training the disease prediction ML model is further based on the group patient data.

In some examples, the processor-executable instructions, when executed by the one or more processors, further facilitate: receiving individual patient data indicating clinical or treatment notes associated with the patient undergoing the dialysis treatment, and wherein determining the disease analysis results is further based on inputting the individual patient data into the disease prediction ML model.

In some variations, the processor-executable instructions, when executed by the one or more processors, further facilitate: obtaining geographical disease data indicating new reported cases of the contagious disease within a geographical area associated with the patient, wherein training the disease prediction ML model is further based on the geographical disease data.

Another exemplary embodiment of the present disclosure provides non-transitory computer-readable medium having processor-executable instructions stored thereon, wherein the processor-executable instructions, when executed, facilitate: receiving, from a medical facility, individual treatment data indicating dialysis treatment information associated with a patient undergoing dialysis treatment; receiving, from a blood testing laboratory, individual lab data indicating blood analysis information associated with the patient; determining disease analysis results for the patient based on inputting the individual treatment data and the individual lab data into a disease prediction machine learning (ML) model, wherein the disease analysis results indicate a likelihood of the patient being infected with a contagious disease; and providing, to the medical facility, instructions indicating one or more responsive actions based on the disease analysis results.

Further features and aspects are described in additional detail below with reference to the FIGS.

BRIEF DESCRIPTION OF THE DRAWINGS

FIG. 6 is another flowchart of another exemplary process for predicting and detecting diseases using the prediction system according to one or more examples of the present application.

DETAILED DESCRIPTION

Exemplary embodiments of the present application leverage information (e.g., treatment data and/or lab data) regularly obtained from dialysis patients to assess and mitigate the spread of infectious disease among dialysis patients. The spread of infectious disease is of particular concern in dialysis clinics and hospitals where dialysis patients are constantly being rotated in and out. Dialysis patients may be immunocompromised due to the chronic kidney disease for which they are receiving dialysis treatment, and it is possible that a patient who is infected with a disease may expose many other vulnerable patients to the disease. In some instances, infectious or contagious diseases may include, but are not limited to, diseases that are transmissible by at least one of the following modes: (a) direct and/or indirect contact; (b) droplets; (c) airborne; and (d) common vehicle.

In particular, exemplary embodiments of the present application are able to predict whether respective dialysis patients may be infected with a disease based on analyzing the treatment data and lab data which is already being gathered for such dialysis patients, allowing preventive actions to be taken early on to avoid the spread of the infectious disease. In an exemplary embodiment of the application, the disease of interest is Coronavirus COVID-19 (also referred to as SARS-CoV-2 or "COVID" for short), which is capable of being spread by asymptomatic or pre-symptomatic individuals infected with the disease. A system (e.g., a prediction system) in accordance with this exemplary embodiment of the application predicts whether dialysis patients are infected with COVID based on regularly obtained treatment data and/or lab data, and based on determining that a respective dialysis patient is infected or likely infected, provides for responsive actions to be taken. The responsive actions may include, for example, adjusting patient scheduling to re-assign the patient to an "isolation shift" for dialysis treatment in which the patient is isolated from other patients and/or ordering a COVID test to be performed on the patient. Other responsive actions may include, for example, initiating a treatment regimen for a patient determined as being infected or likely infected (which may include, for example, administering medication such as antiviral medication to the patient), and/or ordering or allocating personal protective equipment (PPE) for medical facilities based on an amount of infected or likely infected patients being treated by such medical facilities. Another responsive action may include, for example, adjusting dialysis treatment parameters for a patient who is determined as being infected or likely infected (e.g., designating a lower ultrafiltration rate for a patient who is determined as being infected or likely infected).

Figure 1:
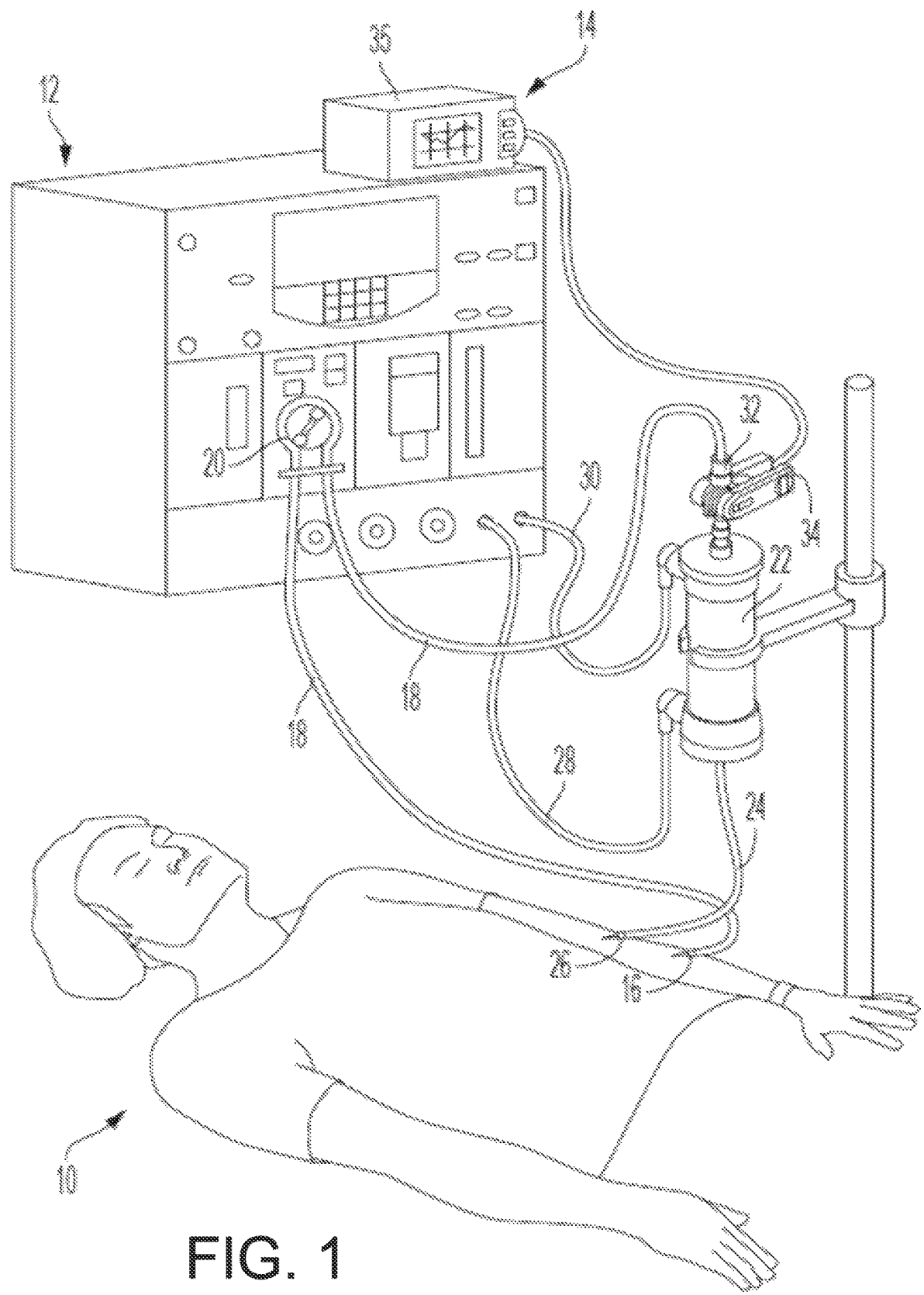
FIG. 1 is a schematic diagram of an exemplary medical treatment system for providing treatment data according to one or more examples of the present application.

FIG. 1 is an exemplary medical treatment system for providing treatment data according to one or more examples of the present application. By way of example, the medical system shown in FIG. 1 is a hemodialysis system; however, other extracorporeal medical systems such as other types of dialysis systems (e.g., peritoneal dialysis (PD) systems) are contemplated and may be configured to provide treatment data for detecting and/or predicting whether dialysis patients are infected with COVID and/or another disease. The hemodialysis system of FIG. 1 and/or other types of medical systems may be used to measure, determine, acquire, and/or obtain treatment data and/or other data associated with a patient 10. The treatment data can include, but is not limited to, blood pressure (standing and/or sitting), weight, temperature, respiration rate, pulse rate, interdialytic weight gain (IDWG), days since last treatment, hematocrit (HCT) levels, hemoglobin (HGB) levels, blood volumes (e.g., absolute blood volumes (ABV)), oxygen saturation values, online clearance (OLC; measure of dialysis adequacy), average small molecule clearance (KECN), and/or other data associated with the patient 10. As will be explained below, the treatment data may be used to determine whether the patient 10 and/or other dialysis patients are infected with COVID and/or another disease.

FIG. 1 depicts a patient 10 undergoing hemodialysis treatment using a hemodialysis machine 12. The hemodialysis system further includes an optical blood monitoring system 14. An inlet needle or catheter 16 is inserted into an access site of the patient 10, such as in the arm, and is connected to extracorporeal tubing 18 that leads to a peristaltic pump 20 and to a dialyzer 22 (or blood filter). The dialyzer 22 removes toxins and excess fluid from the patient's blood. The dialyzed blood is returned from the dialyzer 22 through extracorporeal tubing 24 and return needle or catheter 26. In some parts of the world, the extracorporeal blood flow may additionally receive a heparin drip to prevent clotting. The excess fluids and toxins are removed by clean dialysate liquid which is supplied to the dialyzer 22 via tube 28, and waste liquid is removed for disposal via tube 30. A typical hemodialysis treatment session takes about three to five hours in the United States. Additionally, and/or alternatively, patients in intensive care units (ICUs) may also undergo hemodialysis treatments and/or other dialysis/blood monitoring treatments.

The optical blood monitoring system 14 includes a display device 35 and a sensor device 34. The sensor device 34 may, for example, be a sensor clip assembly that is clipped to a blood chamber 32, wherein the blood chamber 32 is disposed in the extracorporeal blood circuit. A processor (e.g., controller) of the optical blood monitoring system 14 may be implemented in the display device 35 or in the sensor clip assembly 34, or both the display device 35 and the sensor clip assembly 34 may include a respective processor for carrying out respective operations associated with the optical blood monitoring system.

The blood chamber 32 may be disposed in line with the extracorporeal tubing 18 upstream of the dialyzer 22. Blood from the peristaltic pump 20 flows through the tubing 18 into the blood chamber 32. The sensor device 34 includes emitters that emit light at certain wavelengths and detectors for receiving the emitted light after it has passed through the blood chamber 32. For example, the emitters may include LED emitters that emit light at approximately 810 nm, which is isobestic for red blood cells, at approximately 1300 nm, which is isobestic for water, and at approximately 660 nm, which is sensitive for oxygenated hemoglobin, and the detectors may include a silicon photodetector for detecting light at the approximately 660 and 810 nm wavelengths, and an indium gallium arsenide photodetector for detecting light at the approximately 1300 nm wavelength. The blood chamber 32 includes lenses or viewing windows that allows the light to pass through the blood chamber 32 and the blood flowing therein.

An example of an optical blood monitoring system having a sensor clip assembly configured to measure hematocrit and oxygen saturation of extracorporeal blood flowing through a blood chamber is described in U.S. Pat. No. 9,801,993, titled "SENSOR CLIP ASSEMBLY FOR AN OPTICAL MONITORING SYSTEM," which is incorporated by reference in its entirety herein.

A processor of the optical blood monitoring system 14 uses the light intensities measured by the detectors to determine HCT values for blood flowing through the blood chamber 32. The processor calculates HCT, HGB, oxygen saturation, and change in blood volume (e.g., absolute blood volume (ABV)) associated with blood passing through the blood chamber 32 to which the sensor device 34 is attached using one or more models, algorithms, and/or equations. Furthermore, the processor determines additional information such as treatment data for the patient 10.

Figure 2:
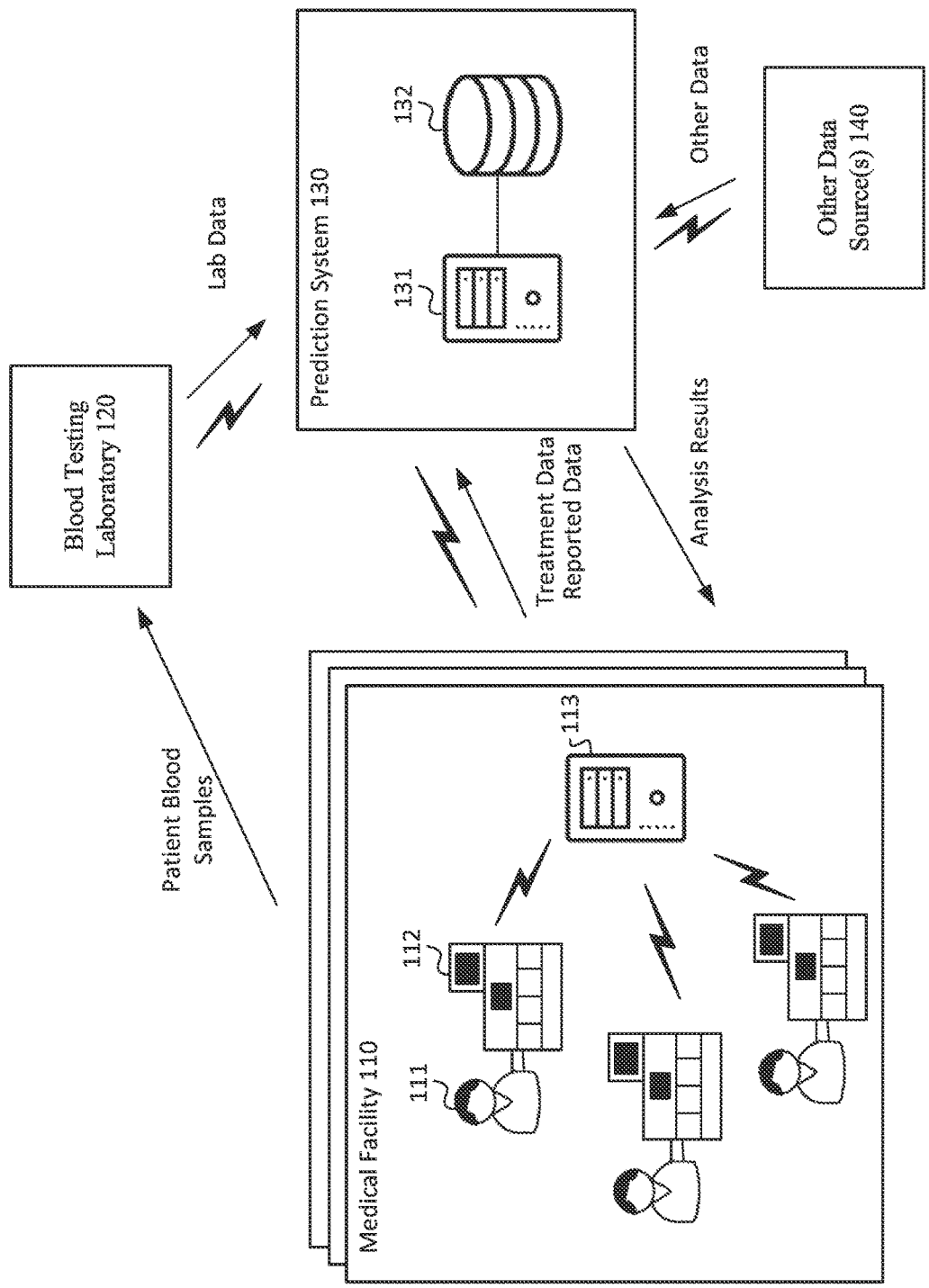
FIG. 2 is a block diagram of an exemplary disease prediction and detection environment according to one or more examples of the present application.

The hemodialysis system depicted in FIG. 1 may be one of a plurality of hemodialysis systems in a dialysis clinic such as the medical facility described in FIG. 2. Patients may come into the dialysis clinic for treatments at regular intervals, for example, on a Monday-Wednesday-Friday schedule or a Tuesday-Thursday-Saturday schedule.

It will be appreciated that the hemodialysis system depicted in FIG. 1 is merely exemplary. The principles discussed herein may be applicable to other medical systems in which treatment data is able to be obtained.

FIG. 2 is a block diagram of an exemplary disease prediction and detection environment 200 according to one or more examples of the present application. The environment 200 includes one or more medical facilities 110 (e.g., dialysis clinics or hospitals), a blood testing laboratory 120, and a prediction system 130.

One or more dialysis patients 111 receive dialysis treatment via one or more dialysis machines 112 at the one or more medical facilities 110, and the one or more medical facilities 110 may further include a computing device 113 in communication with the one or more dialysis machines 112 to obtain patient treatment data. The dialysis patients 111 may include the patient 10 shown in FIG. 1 and the dialysis machines 112 may include and/or be the hemodialysis machine 12 shown and described in FIG. 1, other types of dialysis machines (e.g., PD machines and/or other types of hemodialysis machines), and/or other types of medical systems. The computing device 113 may also obtain treatment data and/or additional patient-reported data via a user interface of the computing device or via communication with one or more other computing devices at the one or more medical facilities 110. Additional patient-reported data may include, for example, patient-reported symptoms such as cough, diarrhea and fever. The computing device 113 is configured to communicate over a network to provide the obtained treatment data and/or the additional reported data to the prediction system 130.

The blood testing laboratory 120 receives and analyzes patient blood samples obtained from the one or more patients 111 via periodic blood draws. Based on analysis of the blood samples, the blood testing laboratory 120 generates lab data which is communicated over a network to the prediction system 130. The lab data can include, but is not limited to, Albumin values, Sodium values, Creatinine values, transferrin saturation (TSAT) values, Potassium values, Phosphorus values, Ferritin values, Urea Reduction Ratio, Calcium values, Calcium (Corrected for serum albumin) values, Bicarbonate values, Intact Parathyroid hormone (PTH) values, Platelet counts, Blood Urea Nitrogen values, White Blood Cell counts, Hemoglobin (HGB) counts, Neutrophils counts, Lymphocytes counts, Monocytes counts, Eosinophils counts, and/or Basophils counts.

Other data from other data sources 140 may also be communicated to the prediction system 130. For example, the prediction system 130 may obtain county-level and/or clinic-level data on COVID reported cases and related mortality. For instance, the other data sources 140 may provide county-level incidence such as new cases per population in a time period (e.g., a 4-day span and/or a 2-week span). Additionally, and/or alternatively, the other data sources may provide clinic-level cases such as new cases reported within a time period (e.g., last 14 days and/or 28 days). In some instances, the prediction system 130 may further obtain information such as vaccine statistics and/or the vaccine status (e.g., whether the patient has had a vaccine associated with the disease) of patients undergoing dialysis treatment.

The prediction system 130 ingests the treatment data, the reported data, the lab data, and/or the other data, for example, by storing the data in a database 132. The prediction system 130 further includes a computing system 131 connected to the database 132, which processes the data using a disease prediction model (e.g., a disease prediction dataset and/or algorithm) to generate analysis results that indicate whether or not respective patients are suspected of being infected. In some instances, the disease prediction model is a machine learning (ML) and/or artificial intelligence (AI) dataset, model, and/or algorithm such as a supervised ML model (e.g., an extreme Gradient Boosting (XGBoost) model) and/or a deep learning model.

In different exemplary embodiments, the analysis results may indicate that the patient is likely positive or negative of a disease (e.g., COVID), may indicate whether the patient is likely positive or negative with a confidence value associated therewith, or may provide various different categorizations and/or classifiers (e.g., labels) for the patient (e.g., strongly suspected positive case, unsure, strongly suspected negative case, and so on).

The analysis results may be written back to the database 132, which may be, for example, an ORACLE database. The analysis results may further be communicated by the prediction system 130 to the one or more medical facilities 110, so that the one or more medical facilities 110 can take appropriate responsive actions. For example, the computing device 113, in response to determining that a particular patient is identified as being positive (or suspected of being positive), may notify a medical provider, order a follow-up test for the patient, and/or adjust patient scheduling by re-assigning the patient to an isolation shift. Notifying a medical provider may include, for example, the analysis results being pushed to electronic medical records (EMR) software which generates alerts to notify medical providers about risks. Ordering follow-up testing and/or adjusting patient scheduling may be implemented via the EMR software as well, for example, through generated tasks with regard to ordering the testing and/or assigning the patient to a designated isolation shift. The EMR software may also be used for other responsive actions, such as initiating a treatment regimen, ordering or allocating PPE, and/or adjusting dialysis treatment parameters. In some instances, the prediction system 130 may receive information from an EMR system that executes the EMR software. In other instances, the prediction system 130 may be the EMR system that executes the EMR software.

In some examples, the prediction system 130 may determine response actions that are to be taken (e.g., notifying a medical provider, ordering a follow-up test for the patient, and/or adjusting patient scheduling), and send instructions to the one or more medical facilities 110 and/or to other entities with respect to executing the responsive actions. These instructions may be sent instead of or in addition to the analysis results.

It will be appreciated that the environment 200 depicted in FIG. 2 is merely exemplary. The principles discussed herein are also applicable to other types of environment and/or system configurations, entities, and equipment.

Figure 3:
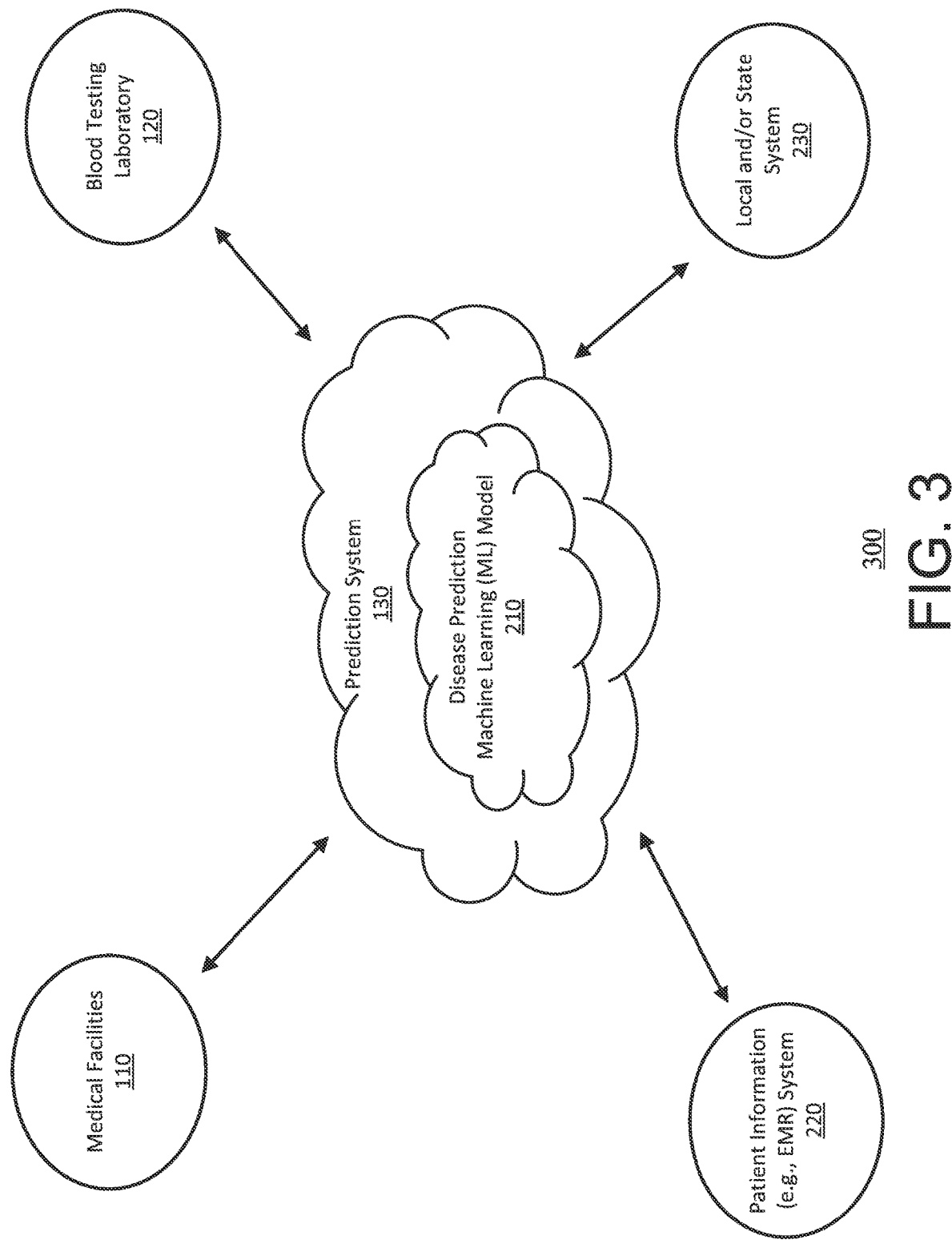
FIG. 3 is a diagram illustrating an exemplary embodiment of systems within the disease prediction and detection environment of FIG. 2 according to one or more examples of the present application.

FIG. 3 is a diagram 300 illustrating an exemplary embodiment of systems within the disease prediction and detection environment 200 according to one or more examples of the present application. For example, the prediction system 130 communicates with one or more entities within the environment 200 such as the medical facilities 110, the blood testing laboratory 120, a patient information (e.g., EMR) system 220, and/or a county and/or state records system 230. The prediction system 130 obtains (e.g., receives and/or retrieves) information from these entities and/or other entities (e.g., from other data sources 140). For instance, the prediction system 130 may obtain treatment data and/or physician data from the medical facilities 110 (e.g., the dialysis machines 112 and/or be the hemodialysis machine 12), lab data from the blood testing laboratory 120, patient data from the patient information (e.g., EMR) system 220, and/or geographical disease data from the local and/or state system 230.

The treatment data and the lab data are described above. The physician data may include, but is not limited to, clinical and/or treatment notes from a dialysis operator (e.g., a doctor, nurse, and/or technician) that is performing and/or assisting with a dialysis treatment for patient (e.g., patient 10 and/or 111). For instance, using a computing device (e.g., computing device 113), the dialysis operator may provide feedback for a patient undergoing the dialysis treatment. The prediction system 130 may obtain this feedback from the medical facilities 110.

The patient data may include, but is not limited to, patient demographics and/or history. For instance, the patient data may include ages, genders, body mass indexes (BMIs) for a plurality of patients. Additionally, and/or alternatively, the patient data may include recent hospital and/or emergency room (ER) visits as well as recent illnesses, infections, and/or diseases for the plurality of patients. The prediction system 130 may obtain the patient demographics and/or history from the patient information system 220. In some instances, the patient information system 220 is an EMR system. In other instances, as described above, the prediction system 130 may be an EMR system and may already have the patient data.

The geographical disease data may include, but is not limited to, local, county, facility, state and/or country information associated with one or more diseases. For example, the geographical disease data may indicate a county-wide level incidence of a disease such as COVID. The county-wide level incidence may be the number of new cases per population over a period of time (e.g., over a four day or two week time span). Additionally, and/or alternatively, the geographical disease data may indicate a population of a particular area and/or the new cases reported over a period of time (e.g., last fourteen or twenty-eight day period) for a particular geographical area such as for a particular medical facility (e.g., the medical facility 110), for the entire county, for the entire state, and/or for the entire country.

Based on obtaining the information from the medical facilities 110, the blood testing laboratory 120, the local and/or state system 230, the patient information system 220, and/or other systems, the prediction system 130 may generate and/or determine a disease prediction ML model 210. For instance, the prediction system 130 may use the treatment data, the physician data, lab data, the patient data, and/or the geographical disease data to train the disease prediction ML model 210. In other words, the prediction system 130 may split the obtained data up into training data and test data (e.g., there is a 60/40, 70/30, 80/20 split for the training data and test data). The prediction system 130 may train the disease prediction ML model using the training data and determine the accuracy of the trained disease prediction ML model using the test data. The prediction system 130 may determine the disease prediction ML model is trained based on the accuracy of the trained disease prediction ML model using a certain threshold (e.g., a 95% threshold and/or an 80% threshold).

The results for using a 95% threshold and an 80% threshold are described below. For example, using a 95% threshold, the trained disease prediction ML data was able to have a 60% accuracy of the predicted positive patients that are actually positive for COVID, 2% of all positive patients are identified as having COVID, 99.9% of negative patients are labelled as negative, 10.8 times more patients are identified as having COVID than if the sampling test dataset was random, and flags 0.2% of the test population (e.g., the test data). Using an 80% threshold, the trained disease prediction ML data was able to have a 36% accuracy of the predicted positive patients that are actually positive for COVID, 23% of all positive patients are identified as having COVID, 97.6% of negative patients are labelled as negative, 6.5 times more patients are identified as having COVID than if the sampling test dataset was random, and flags 3.5% of the test population (e.g., the test data).

In some variations, the prediction system 130 may use supervised learning (e.g., XGBoost and/or Light Gradient Boosting Machine (LightGBM)) to train the disease prediction ML model. In other variations, the prediction system 130 may use a deep learning model (e.g., long short-term memory (LSTM)) to train the disease prediction ML model. In yet other variations, the prediction systems 130 may use an unsupervised learning model to train the disease prediction ML model. Additionally, and/or alternatively, the prediction systems 130 may use multiple of these and/or others as an ensemble to train the disease prediction ML model.

After training the disease prediction ML model, the prediction system 130 stores the trained disease prediction ML data in a database such as database 132. Additionally, and/or alternatively, the prediction system 130 uses the trained disease prediction ML model to determine whether a patient (e.g., patient 10 and/or 111) is infected with a particular disease such as COVID. For example, the prediction system 130 obtains treatment data and/or lab data associated with the patient. The prediction system 130 may input the treatment data and/or lab data into the trained disease prediction ML model to generate an output such as an analysis result, which is described above.

The prediction system 130 includes and/or is implemented using one or more computing devices (e.g., computing device 131), computing platforms, cloud computing platforms, systems, databases (e.g., database 132), servers, and/or other apparatuses capable of predicting whether the patient has a particular disease such as COVID. In some variations, the prediction system 130 may be implemented as engines, software functions, and/or applications. In other words, the functionalities of the prediction system 130 may be implemented as software instructions stored in storage (e.g., memory) and executed by one or more processors.

Figure 4:
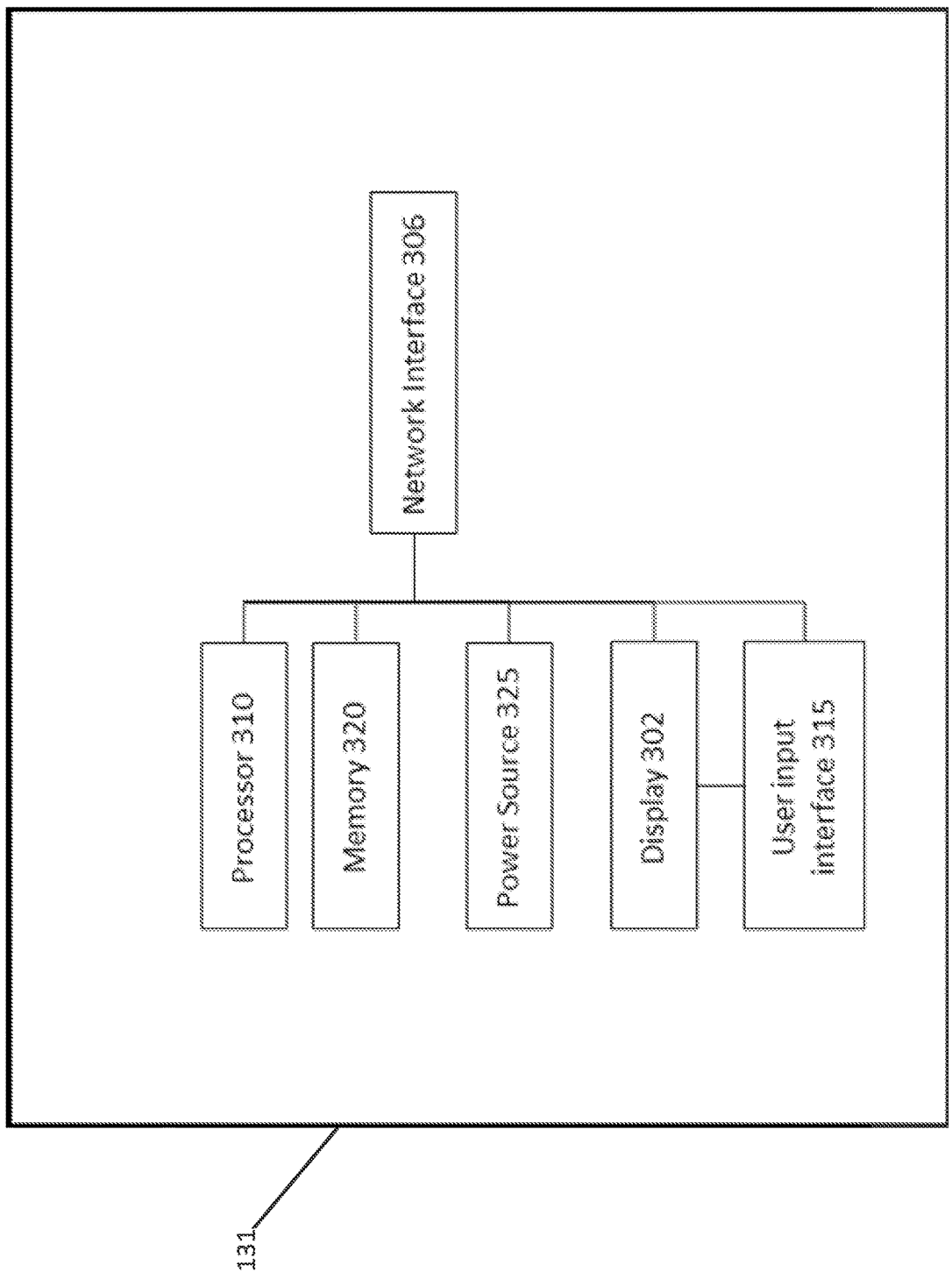
FIG. 4 is a block diagram illustrating an exemplary embodiment of a computing device of a prediction system according to one or more examples of the present application.

FIG. 4 is a block diagram illustrating an exemplary embodiment of a computing device 131 of the prediction system 130 according to one or more examples of the present application. The computing device 131 may include a processor 310 and a memory 320. The processor 310 may receive and/or send control signals to other systems and/or other devices within the prediction system 130 and/or the environment 200. Communication between the processor 310 and other systems may be bi-directional, whereby the systems may acknowledge control signals, and/or may provide information associated with the system and/or requested operations. Additionally, a user input interface 315 and display 302 may be disposed to receive and/or display input from an operator. For instance, the prediction system 130 may use a supervised ML model and the operator may train the supervised ML model using the user input interface 315 and/or the display 302. Examples of the components that may be employed within the user input interface 315 include keypads, buttons, microphones, touch screens, gesture recognition devices, display screens, and speakers. A power source 325 may allow the computing device 131 to receive power, and in some variations may be an independent power source.

The processor 310 may a central processing unit (CPU), controller, and/or logic, that executes computer executable instructions for performing the functions, processes, and/or methods described herein. According to a variety of examples, the processor 310 may be a commercially available processor such as a processor manufactured by INTEL, AMD, MOTOROLA, and FREESCALE. However, the processor 310 may be any type of processor, multiprocessor or controller, whether commercially available or specially manufactured.

The memory 320 may include a computer readable and writeable nonvolatile data storage medium configured to store non-transitory instructions and data. In addition, the memory 320 may include a processor memory that stores data during operation of the processor 310. In some examples, the processor memory includes a relatively high performance, volatile, random access memory such as dynamic random access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 320 may include executable programs or other code that may be executed by the processor 310. The instructions may be persistently stored as encoded signals, and the instructions may cause the processor 310 to perform the functions described herein. The memory 320 may include information that is recorded, on or in, the medium, and this information may be processed by the processor 310 during execution of instructions. A database may be stored in the memory 320, and may be accessible by the processor 310. For example, the trained disease prediction ML model may be stored in memory 320.

The computing device 131 may include a network interface 306 that is used to communicate with other systems and devices within the environment 200 and/or the prediction system 130. In some instances, the network interface 306 may include wireless capabilities so as to wireless communicate with the other systems and devices. In other instances, the network interface 306 may use direct communications to communicate with other systems and devices within the environment 200 and/or the prediction system 130.

Figure 5:
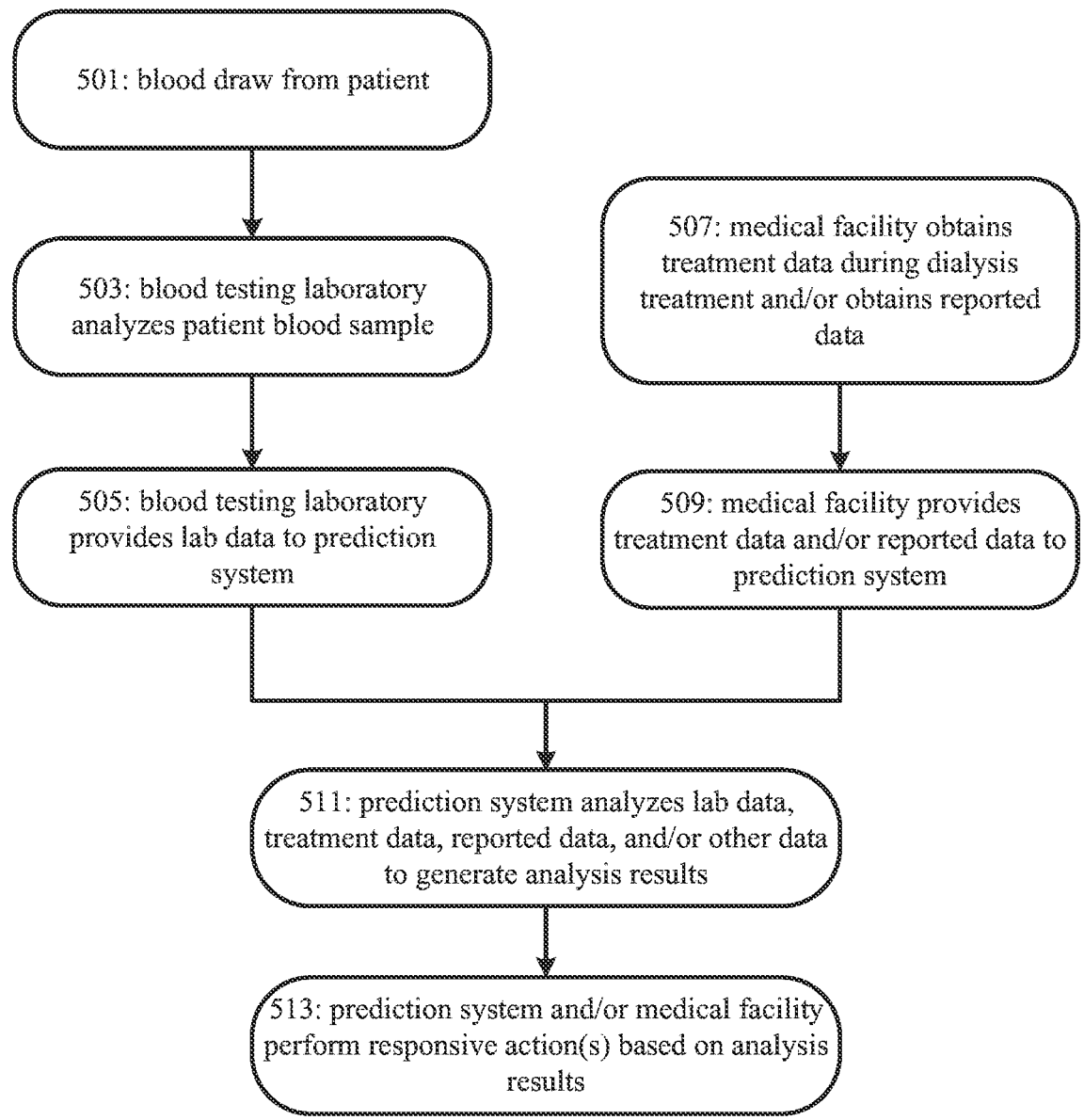
FIG. 5 is a flowchart of an exemplary process for predicting and detecting diseases using the disease prediction and detection environment of FIG. 2 according to one or more examples of the present application.

FIG. 5 is a flowchart of an exemplary process 500 for predicting and detecting diseases using the disease prediction and detection environment of FIG. 2 according to one or more examples of the present application.

At stage 501, a medical professional performs a blood draw on a patient to obtain a patient blood sample. This may be carried out, for example, at a dialysis clinic (e.g., the medical facility 110), and may be repeated on a periodic basis (e.g., weekly or monthly). The patient blood sample is then sent to a blood testing laboratory (e.g., the laboratory 120) for analysis. At stage 503, the blood testing laboratory analyzes the patient blood sample to determine lab data for the patient. At stage 505, the blood testing laboratory provides the lab data to the prediction system 130 (or to a medical provider who inputs the lab data into the prediction system). For example, a laboratory instrument may directly communicate directly reportable lab results to a laboratory information management system which is in communication with the prediction system or with the medical provider, or a lab technician may enter the lab data into a computing device at the blood testing laboratory which uploads the lab data to the prediction system through a communication network. The prediction system may store the lab data, together with lab data of other patients and historical lab data, in a database.

At stage 507, a medical facility obtains treatment data of a patient during dialysis treatment and/or obtains patient-reported data. The treatment data may be obtained automatically, for example, via a dialysis machine (e.g., the dialysis machine 12 and/or 112) and communicated to a computing device (e.g., computing device 113) of the medical facility. The treatment data may also be obtained based on a medical provider entering the treatment data into the computing device of the medical facility. The patient-reported data (e.g., the patient data) may be provided by the patient and/or by a medical provider to a computing device of the medical facility. At stage 509, the medical facility provides the treatment data and/or the patient data to the prediction system, for example, by communicating over a network. In some instances, the patient and/or a medical provider may directly provide treatment data and/or patient-reported data to the prediction system over the network.

At stage 511, the prediction system analyzes lab data, treatment data, reported data, and/or other data to generate analysis results. The analysis at stage 511 may be based on using a disease prediction model (e.g., a disease prediction ML model). In some examples, the disease prediction model is associated with one or more diseases or infections such as COVID. In other words, the disease prediction model may make predictions indicating whether one or more patients are believed to have COVID. For instance, the output from the disease prediction model may indicate a classification (e.g., the patient is positive for COVID, is negative for COVID, is most likely positive for COVID, a probability that the patient has COVID, and so on).

The disease prediction model may be updated as new data flows into the prediction system. The data which is fed into the model may be preprocessed in an automated manner, and the model may ingest data at regular intervals. The analysis results generated by the prediction system for each patient may be in the form of an ordered list of risk scores and associated reasons (variables) driving the scores. The analysis results may also include a prediction for the patient, which may or may not include a confidence score associated therewith. The confidence score may be between 0 to 1. For instance, a confidence value of 0.99 may indicate that the disease prediction model is 99% certain that the patient has COVID. Once the prediction and any additional information relating to the prediction has been generated, the information can be written into a database of the prediction system, from which the analysis results are disseminated to medical providers via automatic processing (e.g., via an EMR system).

The dissemination of the analysis results may be part of stage 513. Stage 513 includes the prediction system and/or the medical facility performing one or more responsive actions based on the analysis results generated by the prediction system. As discussed above, the responsive actions may include, for example, notifying medical providers, ordering follow-up testing, re-assigning patients to isolation shifts, initiating a treatment regimen, ordering or allocating PPE, and/or adjusting dialysis treatment parameters.

In some instances, the prediction system may perform one or more responsive actions such as notify a medical provider (e.g., the medical facility 110) of the analysis results (e.g., the output of the disease prediction model indicating the patient has a particular disease). For instance, the prediction system may provide instructions to cause display of a prompt at a computing device (e.g., computing device 113) indicating the analysis results. For example, the prompt may indicate that the patient 111 likely has COVID and provide a probability (e.g., 95%) that the patient 111 has COVID.

In some examples, the prediction system and/or the medical facility may perform one or more responsive actions in order to re-assign a patient to an isolation shift based on the analysis results (e.g., the output of the disease prediction model indicating the patient has a particular disease). For instance, the prediction system may provide instructions to the medical facility and/or another server that has a scheduling program and/or application. The instructions may indicate for the scheduling program and/or application to isolate the patient for one or more dialysis treatment sessions.

In some variations, the prediction system and/or the medical facility may perform one or more responsive actions such as ordering follow-up testing based on the analysis results (e.g., the output of the disease prediction model indicating the patient has a particular disease). For instance, the prediction system may provide instructions to the medical facility and/or another system/server indicating for the medical facility/other system to perform follow-up testing due to the analysis results such as analysis results indicating the patient has COVID. In some instances, the instructions to the medical facility may cause a computing device (e.g., computing device 113) to display a prompt indicating that due to the analysis results, the patient should undergo follow-up testing. In other instances, the prediction system may provide instructions indicating for a scheduling program and/or application associated with the medical facility 110 and/or another system to directly schedule one or more follow-up testing based on the analysis results.

In some examples, based on the analysis results (e.g., the output of the disease prediction model indicating the patient has a particular disease), the prediction system and/or the medical facility may perform one or more responsive actions such as initiating a treatment regimen and/or adjusting one or more dialysis treatment parameters. For instance, the prediction system may provide instructions to the medical facility and/or another system/server indicating for the medical facility/other system to perform follow-up testing due to the analysis results such as analysis results indicating the patient has COVID. In some instances, the instructions to the medical facility may cause a computing device (e.g., computing device 113) to display a prompt indicating that due to the analysis results, the patient should undergo a particular treatment regimen and/or the dialysis treatment parameters for the patient should be adjusted. In other instances, the prediction system may provide instructions indicating for a scheduling program and/or application associated with the medical facility 110 and/or another system to schedule a particular treatment regimen for the patient and/or to change the dialysis treatment parameters for the patient.

In some variations, the prediction system may perform one or more responsive actions such as ordering more PPE based on the analysis results (e.g., the output of the disease prediction model indicating the patient has a particular disease). For instance, the prediction system may provide instructions to cause display of a prompt at a computing device (e.g., computing device 113) indicating for the medical facility to order more PPE based on the analysis results. In some instances, the prediction system may provide the instructions to another system such as a PPE provider to order more PPE for the medical facility.

Training the COVID prediction model which is used in stage 511 may include the following operations:

1. Extracting treatment data, lab data, and reported data from databases/systems (such as EMR databases of an EMR system such as the patient information system 220), and extracting other data (such as geographical disease data) from other data sources (e.g., an external, open data source such as the local and/or state system 230).

2. Aggregating lab data and treatment data for dialysis patients, for example, on a weekly basis. The most recent lab panel and week of dialysis treatments for each respective patient is used, along with changes between recent results relative to prior weeks (historical data).

3. Adding other data (such as county-level population data on reported COVID positive numbers) to patient-level data based on the patient's place of residence and/or the geographical region of the medical facility where the patient received the dialysis treatment.

4. Feeding a subset of the data ('training' data) into a disease prediction ML model such as an XGBoost classifier, where patients with positive COVID tests are labeled, for example, with a 1 and known or presumed negative patients are labeled, for example, with a 0. Each patient provides a single set of observations consisting of the elements in steps 2-3 above. The XGBoost classifier takes these inputs and constructs a number of decision trees. Each decision tree is given a random sample of the training set variables and observations and constructs a series of thresholds to split the variables on in order to maximize the information gained from each split. For example, the first split might be made to separate observations by temperature above or below 98.6° F., followed by additional splits for each separated set of observations. Trees are constructed iteratively and new trees are added to predict the errors of previous trees. Once all decision trees have been constructed, after reaching the maximum allowed number of trees or performance no longer improves with the addition of more trees, this ensemble of decision trees effectively makes up the final model. In some instances, the prediction system may put more significance on certain sets of data (e.g., the prediction may be influenced more by certain sets of data and/or more decision trees may use certain sets of data) as opposed to other sets of obtained data. For instance, the prediction system may be more influenced by and/or may use more frequently the geographical disease data (e.g., the reported number of cases for the medical facility and for the as compared to some other sets of data such as treatment data. Additionally, and/or alternatively, the prediction system may be more influenced by and/or may use more frequently the patient data (e.g., BMI) as compared to the treatment data, but still less frequently than the geographical disease data.

5. The performance of the XGBoost classifier is verified using a separate portion of the data that was not used in the training such as a validation dataset. The validation dataset includes patient-level observations that are fed into the model where for each patient, the data is passed through the individual decision trees, which all 'vote' on the most likely classification, resulting in a predicted probability of that patient being in the positive class. Performance is measured by looking at several metrics, for example, the number of true positives correctly identified (recall) and the number of predicted positives actually positive (precision). If model performance does not meet acceptable goals, model hyperparameters (e.g. maximum number of trees or number of splits a tree may construct) may be tuned (different values tried) to find optimal parameters and the model is then retrained.

Once the XGBoost classifier has been trained and the performance has been verified, the XGBoost classifier is ready to be used in stage 511 to generate analysis results for dialysis patients as treatment data, lab data, reported data, and/or other data flows into the prediction system. Predictions follow a similar pattern as testing performance in step 4, except performance is not calculated as the ground truth is unknown at this stage. When the ground truth does become known, the ground truth for patients in combination with the patient-level data may be used in further training and refinement of the model.

FIG. 6 is another flowchart of another exemplary process 600 for predicting and detecting diseases using the prediction system according to one or more examples of the present application. Process 600 may describe similar stages to process 500 described above except process 600 describes it from the perspective of a back-end system such as the prediction system 130.

In operation, at stage 602, the prediction system 130 receives, from a medical facility 110, treatment data indicating dialysis treatment information associated with a patient undergoing dialysis treatment. As mentioned above, the treatment data may include, but is not limited to, can include, but is not limited to, blood pressure, weight, temperature, respiration rate, pulse rate, interdialytic weight gain, days since last treatment, hematocrit (HCT) levels, hemoglobin (HGB) levels, blood volumes (e.g., absolute blood volumes (ABV)), oxygen saturation values, and/or other data associated with a particular patient.

At stage 604, the prediction system 130 receives, from a blood testing laboratory 120, lab data indicating blood analysis information associated with the patient. For instance, as mentioned above, the lab data may include, but is not limited to, Albumin values, Sodium values, Creatinine values, transferrin saturation (TSAT) values, Potassium values, Phosphorus values, Ferritin values, Urea Reduction Ratio, Calcium values, Calcium (Corrected) values, Bicarbonate values, Intact Parathyroid hormone (PTH) values, Platelet counts, Blood Urea Nitrogen values, White Blood Cell counts, Hemoglobin counts, Neutrophils counts, Lymphocytes counts, Monocytes counts, Eosinophils counts, and/or Basophils counts.

Additionally, and/or alternatively, the prediction system 130 may receive further information associated with the patient, the medical facility 110, and/or the geographical area associated with the medical facility 110 and/or patient. For instance, the prediction system 130 may receive physician data (e.g., notes regarding the patient undergoing the dialysis treatment) from the medical facility 110, patient data of the patient (e.g., the age, gender, BMI, recent hospitalization/ER visits, recent illnesses, infections, and/or other patient demographic or patient history data), and/or geographical disease data (e.g., the number of new cases or new cases per population for a particular geographical area associated with the patient and/or the medical facility 110).

At stage 606, the prediction system 130 determines disease analysis results for the patient based on inputting the treatment data and the lab data into a disease prediction machine learning (ML) model. For example, as mentioned above, the prediction system 130 may train and/or store a disease prediction ML model using obtained information. After training the disease prediction ML model, at stage 606, the prediction system 130 may input information associated with a patient (e.g., the patient's lab data and/or the patient's treatment data) into the trained disease prediction ML model to determine an output from the trained disease prediction ML model. The output may be the disease analysis results such as may indicate that the patient is likely positive or negative of a disease (e.g., COVID), may indicate whether the patient is likely positive or negative with a confidence value associated therewith, or may provide various different categorizations and/or classifiers for the patient.

Additionally, and/or alternatively, the prediction system 130 may input additional and/or alternative information or data into the trained disease prediction ML model. For instance, the prediction system 130 may input the physician data, the patient data, and/or the geographical disease data into the trained disease prediction ML model. By inputting further data into the trained disease prediction ML model, the prediction system 130 may more accurately predict whether the patient has a particular disease such as COVID. For instance, based on inputting the treatment data and the lab data, the prediction system 130 may determine the patient has COVID with a probability value of 90% (e.g., 0.9). Based on further inputting the geographical disease data and/or the patient data, this probability value may increase to 95% (e.g., 0.95). In some instances, even if certain aspects or types of data are missing (e.g., portions of the patient data such as BMI), the prediction system 130 may still determine an output such as predicting whether the patient has a particular disease.

At stage 608, the prediction system 130 provides, to the medical facility 110, instructions indicating one or more responsive actions based on the disease analysis results. The responsive actions may include, but is not limited to, order a follow-up test for the patient, ordering or allocating more PPE, and/or adjust patient scheduling by re-assigning the patient to an isolation shift.

In some instances, prior to stage 606, the prediction system 130 may train the disease prediction ML model. For instance, the prediction system 130 may obtain information such as the treatment data, the physician data, the lab data, the patient data, the geographical disease data, and/or additional information. Using the obtained information, the prediction system 130 may train the disease prediction ML model such that the disease prediction ML model is capable of determining whether a patient has one or more diseases such as COVID. In some examples, the prediction system 130 may train the disease prediction ML model using the treatment data and the lab data. In other examples, the prediction system 130 may train the disease prediction ML model using treatment data, lab data, and further information such as the physician data and/or the patient data. In yet other examples, the prediction system 130 may use all of the obtained information (e.g., the treatment, physician, lab, patient, and geographical disease data) to train the disease prediction ML model.

In some examples, the prediction system 130 may train multiple disease prediction ML model such that each of the disease prediction ML model is associated with a particular geographical area and/or a medical facility. For instance, the prediction system 130 may obtain treatment data, lab data, physician data, geographical disease data, and/or other data associated with a particular medical facility (e.g., medical facility 110). The prediction system 130 may use the data associated with (e.g., obtained from) the particular medical facility to train a disease prediction ML model for the medical facility. Further, the prediction system 130 may use the data associated with another (e.g., second) medical facility to train a second disease prediction ML model for the other medical facility. These two disease prediction ML models may have some similarities (e.g., certain trees may be the same), but may also have some differences (e.g., certain trees may be slightly and/or significantly different). After training the plurality of disease prediction ML models, the prediction system 130 and/or other systems may perform process 500 and/or 600 described above. Further, the prediction system 130 may select a particular disease prediction ML model from the plurality of trained disease prediction ML models to use for the patient. For instance, a particular medical facility 110 may be associated with a first disease prediction ML model and the medical facility 110 may provide treatment data for a particular patient to the prediction system 130. In such instances, the prediction system 130 may use the first disease prediction ML model to determine whether the particular patient is positive or negative for a disease such as COVID.

In some variations, the prediction system 130 may re-train one or more disease prediction ML models. For instance, the prediction system 130 may receive and/or obtain information such feedback. The feedback may indicate for the prediction system 130 to re-train a particular disease prediction ML model and/or indicate that a particular disease prediction ML model has been inaccurate one or more times. For example, the geographical disease data may change over time (e.g., a particular geographical region may have ten cases over a first month and then two thousand cases over the second month or alternatively, a different variant of the disease may be encountered in the particular geographical region after a certain period of time). Based on this change, a disease prediction ML model that was trained using the first month's data might not be accurate in the second month to detect whether a patient is positive or negative for COVID. As such, the prediction system 130 may obtain feedback from the medical facilities 110 indicating that their disease prediction ML model is faulty and/or is producing inaccuracies. Based on this feedback, the prediction system 130 may re-train the disease prediction ML models. The prediction system 130 may re-train the disease prediction ML models using more relevant (e.g., up to date) data. For instance, the prediction system 130 may use the data such as the geographical disease data from the previous two weeks. After re-training the disease prediction ML models, the prediction system 130 and/or other systems may perform process 500 and/or 600 described above.

In some instances, this re-training may be automated. For instance, based on receiving a certain number of instances (e.g., 200) or a certain percentage (e.g., 10%) of cases indicating that the disease prediction ML model is inaccurate, the prediction system 130 may re-train the disease prediction ML model. In other instances, the prediction system 130 may re-train the disease prediction ML model based on operator feedback.

A COVID prediction model in accordance with an exemplary implementation of the prediction system was demonstrated as being effective. The exemplary results obtained using the COVID prediction model described herein are described in further detail in U.S. Provisional Patent Application Ser. No. 63/008,626, filed Apr. 10, 2020, entitled "SYSTEM FOR ASSESSING AND MITIGATING POTENTIAL SPREAD OF INFECTIOUS DISEASE AMONG DIALYSIS PATIENTS," the contents of which application is expressly incorporated by reference herein.

Furthermore, it will be appreciated that a threshold score for generating a positive prediction for a patient may be adjusted based on balancing the capability of the model to detect true positive cases versus the desire to avoid false positives. A high true positive rate may be selected while still maintaining a low false positive rate are shown in the appendix of the U.S. Provisional Patent Application Ser. No. 63/008,626.

In some examples, a PYTHON version may be used to build the disease prediction ML model utilizing XGBoost. The XGBoost PYTHON package used input variables from the training model to construct multiple decision trees, giving each a random sample, and established a series of thresholds that split variables to maximize the information gain. The decision trees were constructed iteratively, and new decision trees were added to predict prior errors. The decision trees made by the XGBoost ML model are able to handle missing values without imputation by including their presence when determining the splits (e.g., splitting observations with temperatures greater than or equal to 98.0 degrees fahrenheit from temperatures less than 98.0 degrees fahrenheit or missing temperature). After no or little further improvements in performance were achieved using the validation dataset (also used for hyperparameter tuning), the ensemble of decision trees produced by the final ML model that was assessed with the testing dataset.

In some instances, the disease prediction ML model may be trained using a plurality (e.g., 81) selected treatment/laboratory variables up to the individually defined prediction date (e.g., 3 days prior to the index date or the testing date of a HD patient having COVID) to predict the risk of a COVID infection being identified in the following 3 or more days. This may yield individual predictions at least 3 days in advance of symptoms that warranted testing. The testing data may be randomly split into 60, 20, and 20 for training, validation, and testing datasets respectively. Then, the same number of COVID negative patients may be added to the training and validation datasets. The testing dataset used to evaluate the final model performance may have a higher number of COVID negative samples added.

In some variations, the performance of the disease prediction ML model may be measured by area under the receiver operating characteristic curve (AUROC) in the training, validation, and testing datasets, as well as the recall, precision, and lift in the testing datasets. Additionally, and/or alternatively, the area under the precision-recall curve (AUPRC) may also be used to evaluate the testing dataset.

AUROC may measure the rate of true and false positives classified by the prediction model across probability thresholds. Recall (sensitivity) may measure the rate of true positives classified by the model at a specified threshold and may be calculated as follows: Recall=number of true positives classified by model/(number of true positives classified by model+number of false negatives classified by model).

Precision measures the positive predictive value for the model at a specified threshold may be calculated as follows: Precision=number of true positives classified by model/(number of true positives classified by model+number of false positives classified by model). Lift measures the effectiveness of the model compared to random sampling and may be calculated as follows: Lift=model precision/proportion of positives in dataset. AUPRC measures the ratio of precision for corresponding recall values across probability thresholds. AUROC, AUPRC, recall, and precision metrics may yield scores on a scale of 0 (lowest) to 1 (highest). The cutoff threshold for classifying predictions may be selected to optimize recall, precision, and lift according to a particular use case.

An exemplary implementation of the present application of using a disease prediction ML model was described, developed, used, tested, and successfully validated (e.g., using retrospective data and/or results) that appears to have suitable performance in identifying dialysis patients at risk of having an undetected COVID infection that is later identified. This is described in further detail in Monaghan, Caitlin, et al., "Machine Learning for Prediction of Hemodialysis Patients with an Undetected SARS-CoV-2 Infection," available at kidney360.asnjournals.org, which is hereby incorporated by reference herein.

It will be appreciated that the various machine-implemented operations described herein may occur via the execution, by one or more respective processors, of processor-executable instructions stored on a tangible, non-transitory computer-readable medium, such as a random access memory (RAM), read-only memory (ROM), programmable read-only memory (PROM), and/or another electronic memory mechanism. Thus, for example, operations performed by any device described herein may be carried out according to instructions stored on and/or applications installed on the device, and via software and/or hardware of the device.

All references, including publications, patent applications, and patents, cited herein are hereby incorporated by reference to the same extent as if each reference were individually and specifically indicated to be incorporated by reference and were set forth in its entirety herein.

While the application has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present application covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A method, comprising:
training, by a prediction system, a first disease prediction machine learning (ML) model based on geographical disease data indicating new reported cases of a contagious disease within a first geographical area;
receiving, by the prediction system and from a medical facility, individual treatment data indicating dialysis treatment information associated with a patient undergoing an initial dialysis treatment, wherein the medical facility is associated with the first geographical area;
receiving, by the prediction system and from a blood testing laboratory, individual lab data indicating blood analysis information associated with the patient;
determining, by the prediction system, disease analysis results for the patient based on inputting the individual treatment data and the individual lab data into the first disease prediction ML model, wherein the disease analysis results indicate a likelihood of the patient being infected with the contagious disease;
providing, by the prediction system and to the medical facility, instructions indicating one or more responsive actions based on the disease analysis results, wherein the one or more responsive actions comprise lowering an ultrafiltration rate for the patient to use for a subsequent dialysis treatment;
performing, by a dialysis machine located at the medical facility, the subsequent dialysis treatment for the patient using the lowered ultrafiltration rate;
receiving, by the prediction system and from the medical facility, feedback information indicating a plurality of inaccuracy counts associated with the disease analysis results; and
based on comparing the plurality of inaccuracy counts with one or more thresholds, re-training, by the prediction system, the first disease prediction ML model.

2. The method of claim 1, further comprising:
receiving, by the prediction system, group treatment data indicating dialysis treatment information associated with a plurality of patients undergoing the initial dialysis treatment; and
receiving, by the prediction system, group lab data indicating blood analysis information associated with the plurality of patients undergoing the initial dialysis treatment, wherein training the first disease prediction ML model is further based on the group treatment data and the group lab data.

3. The method of claim 2, further comprising:
receiving, by the prediction system, group physician data indicating clinical or treatment notes associated with the plurality of patients undergoing the initial dialysis treatment,
wherein training the first disease prediction ML model is further based on the group physician data.

4. The method of claim 3, further comprising:
receiving, by the prediction system and from the medical facility, individual physician data indicating clinical or treatment notes associated with the patient undergoing the initial dialysis treatment, and
wherein determining the disease analysis results is further based on inputting the individual physician data into the first disease prediction ML model.

5. The method of claim 2, further comprising:
obtaining, by the prediction system, group patient data indicating patient demographics and history associated with the plurality of patients undergoing the initial dialysis treatment,
wherein training the first disease prediction ML model is further based on the group patient data.

6. The method of claim 5, further comprising:
receiving, by the prediction system, individual patient data indicating clinical or treatment notes associated with the patient undergoing the initial dialysis treatment, and
wherein determining the disease analysis results is further based on inputting the individual patient data into the first disease prediction ML model.

7. The method of claim 2, wherein the group treatment data is associated with the medical facility and the geographical disease data further indicates new reported cases of the contagious disease within a second geographical area, and wherein the method further comprises:
training, by the prediction system and based on the geographical disease data, a second disease prediction ML model for a second medical facility that is within the second geographical area;
determining that the individual treatment data is from the medical facility that is associated with the first geographical area; and
selecting to use the first disease prediction ML model for the patient rather than the second disease prediction ML model based on determining that the individual treatment data is from the medical facility that is associated with the first geographical area.

8. The method of claim 7, wherein the first disease prediction ML model is a first eXtreme Gradient Boosting (XGBoost) model comprising a plurality of first decision trees and the second disease prediction ML model is a second XGBoost model comprising a plurality of second decision trees that are different from the plurality of first decision trees.

9. The method of claim 8, wherein training the first disease prediction ML model comprises generating the plurality of first decision trees, wherein training the second disease prediction ML model comprises generating the plurality of second decision trees, and wherein a set of decision trees from the plurality of second decision trees are different from decision trees within the plurality of first decision trees based on the geographical disease data indicating different newly reported cases of the contagious disease within the first geographical area and the second geographical area.

10. The method of claim 1, wherein the first disease prediction ML model is a deep learning model.

11. The method of claim 1, wherein the one or more responsive actions further comprise initiating a treatment regimen for the patient, allocating personal protective equipment (PPE) for the medical facility, or adjusting patient scheduling to re-assign the patient to an isolation shift for the subsequent dialysis treatment.

12. A prediction system, comprising:
one or more processors; and
a non-transitory computer-readable medium having processor-executable instructions stored thereon, wherein the processor-executable instructions, when executed by the one or more processors, facilitate:
training a first disease prediction machine learning (ML) model based on geographical disease data indicating new reported cases of a contagious disease within a first geographical area;
receiving, from a medical facility, individual treatment data indicating dialysis treatment information associated with a patient undergoing initial dialysis treatment, wherein the medical facility is associated with the first geographical area;
receiving, from a blood testing laboratory, individual lab data indicating blood analysis information associated with the patient;
determining disease analysis results for the patient based on inputting the individual treatment data and the individual lab data into the first disease prediction ML model, wherein the disease analysis results indicate a likelihood of the patient being infected with the contagious disease;
providing, to the medical facility, instructions indicating one or more responsive actions based on the disease analysis results, wherein the one or more responsive actions comprise lowering an ultrafiltration rate for the patient to use for a subsequent dialysis treatment, wherein a dialysis machine located at the medical facility performs the subsequent dialysis treatment for the patient using the lowered ultrafiltration rate;
receiving, from the medical facility, feedback information indicating a plurality of inaccuracy counts associated with the disease analysis results; and
based on comparing the plurality of inaccuracy counts with one or more thresholds, re-training the first disease prediction ML model.

13. The prediction system of claim 12, wherein the processor-executable instructions, when executed by the one or more processors, further facilitate:
receiving group treatment data indicating dialysis treatment information associated with a plurality of patients undergoing the initial dialysis treatment; and
receiving group lab data indicating blood analysis information associated with the plurality of patients undergoing the initial dialysis treatment,
wherein training the first disease prediction ML model is further based on the group treatment data and the group lab data.

14. The prediction system of claim 13, wherein the processor-executable instructions, when executed by the one or more processors, further facilitate:
receiving group physician data indicating clinical or treatment notes associated with the plurality of patients undergoing the initial dialysis treatment,
wherein training the first disease prediction ML model is further based on the group physician data.

15. The prediction system of claim 14, wherein the processor-executable instructions, when executed by the one or more processors, further facilitate:
- receiving, from the medical facility, individual physician data indicating clinical or treatment notes associated with the patient undergoing the initial dialysis treatment, and
- wherein determining the disease analysis results is further based on inputting the individual physician data into the first disease prediction ML model.

16. The prediction system of claim 13, wherein the processor-executable instructions, when executed by the one or more processors, further facilitate:
- obtaining group patient data indicating patient demographics and history associated with the plurality of patients undergoing the initial dialysis treatment,
- wherein training the first disease prediction ML model is further based on the group patient data.

17. The prediction system of claim 16, wherein the processor-executable instructions, when executed by the one or more processors, further facilitate:
- receiving individual patient data indicating clinical or treatment notes associated with the patient undergoing the initial dialysis treatment, and
- wherein determining the disease analysis results is further based on inputting the individual patient data into the first disease prediction ML model.

18. A non-transitory computer-readable medium having processor-executable instructions stored thereon, wherein the processor-executable instructions, when executed, facilitate:
- training a first disease prediction machine learning (ML) model based on geographical disease data indicating new reported cases of a contagious disease within a first geographical area;
- receiving, from a medical facility, individual treatment data indicating dialysis treatment information associated with a patient undergoing initial dialysis treatment, wherein the medical facility is associated with the first geographical area;
- receiving, from a blood testing laboratory, individual lab data indicating blood analysis information associated with the patient;
- determining disease analysis results for the patient based on inputting the individual treatment data and the individual lab data into the first disease prediction ML model, wherein the disease analysis results indicate a likelihood of the patient being infected with the contagious disease;
- providing, to the medical facility, instructions indicating one or more responsive actions based on the disease analysis results, wherein the one or more responsive actions comprise lowering an ultrafiltration rate for the patient to use for a subsequent dialysis treatment, wherein a dialysis machine located at the medical facility performs the subsequent dialysis treatment for the patient using the lowered ultrafiltration rate;
- receiving, from the medical facility, feedback information indicating a plurality of inaccuracy counts associated with the disease analysis results; and
- based on comparing the plurality of inaccuracy counts with one or more thresholds, re-training, by the prediction system, the first disease prediction ML model.

* * * * *